US010051858B2

(12) United States Patent
Ileleji et al.

(10) Patent No.: US 10,051,858 B2
(45) Date of Patent: *Aug. 21, 2018

(54) APPARATUS AND METHOD FOR PRODUCING BIOBASED CARRIERS FROM BYPRODUCTS OF BIOMASS PROCESSING

(71) Applicant: Purdue Research Foundation, West Lafayette, IN (US)

(72) Inventors: Klein E. Ileleji, West Lafayette, IN (US); Kyle V. Probst, Bloomington, IN (US)

(73) Assignee: Purdue Research Foundation, West Lafayette, IN (US)

( * ) Notice: Subject to any disclaimer, the term of this patent is extended or adjusted under 35 U.S.C. 154(b) by 279 days.

This patent is subject to a terminal disclaimer.

(21) Appl. No.: 14/939,196

(22) Filed: Nov. 12, 2015

(65) Prior Publication Data

US 2016/0135449 A1 May 19, 2016

Related U.S. Application Data

(60) Division of application No. 13/106,515, filed on May 12, 2011, now Pat. No. 9,272,468, which is a
(Continued)

(51) Int. Cl.
*B01F 7/04* (2006.01)
*B29C 67/02* (2017.01)
(Continued)

(52) U.S. Cl.
CPC ........... *A01N 25/002* (2013.01); *A01N 25/08* (2013.01); *A23K 1/002* (2013.01); *A23K 1/06* (2013.01);
(Continued)

(58) Field of Classification Search
CPC .... C03C 1/026; C09C 1/58; B01J 2/10; B01J 2/12; B01J 2/14; B01J 2/20; B01J 2/28;
(Continued)

(56) References Cited

U.S. PATENT DOCUMENTS 1,921,114 A * 8/1933 Brackelsberg ........ C22B 1/2406
100/904
2,457,962 A * 1/1949 Whaley .................... C08K 9/08
23/314
(Continued)

*Primary Examiner* — Seyed Masoud Malekzadeh
(74) *Attorney, Agent, or Firm* — Hartman Global IP Law; Gary M. Hartman; Domenica N. S. Hartman

(57) ABSTRACT

An apparatus for producing biobased carriers for dispersal of biological and chemical molecules includes a premixer having a first inlet, a first outlet, a cavity configured for receiving a wet coproduct and a binder through the first inlet, and a stirring apparatus within the cavity for premixing the wet coproduct and binder into a substantially homogeneous mixture; a high shear mixer having a housing, a drive apparatus and a high shear apparatus, the housing defining an opening, the drive apparatus being within the housing and for forcing the substantially homogeneous mixture from the premixer into the high shear apparatus, and the high shear apparatus including a rotor, a stator and a screen covering the opening and being for shear mixing the mixture including forcing the mixture through the screen and out of the housing in the form of nucleation enhanced particles; and an agglomerator having an interior chamber sized and configured to receive the nucleation enhanced particles from the high shear mixer and for transforming the nucleation enhanced particles into substantially spherical biomass pellets.

20 Claims, 7 Drawing Sheets

Related U.S. Application Data continuation-in-part of application No. 12/418,565, filed on Apr. 3, 2009, now Pat. No. 8,118,582.

(60) Provisional application No. 61/042,046, filed on Apr. 3, 2008.

(51) Int. Cl.

| | | |
|---|---|---|
| *A01N 25/00* | (2006.01) | |
| *B01F 13/10* | (2006.01) | |
| *B01J 2/12* | (2006.01) | |
| *B01F 7/02* | (2006.01) | |
| *B01J 2/10* | (2006.01) | |
| *B01F 7/00* | (2006.01) | |
| *A01N 25/08* | (2006.01) | |
| *A23K 1/00* | (2006.01) | |
| *A23K 1/06* | (2006.01) | |
| *A23K 1/16* | (2006.01) | |
| *A61K 9/16* | (2006.01) | |
| *C22B 1/24* | (2006.01) | |
| *B29B 9/08* | (2006.01) | |
| *B29C 47/26* | (2006.01) | |
| *B29C 47/36* | (2006.01) | |
| *B29B 13/10* | (2006.01) | |
| *B29C 47/60* | (2006.01) | |
| *B29C 67/08* | (2006.01) | |
| *B01J 2/28* | (2006.01) | |
| *B29C 47/38* | (2006.01) | |
| *B01J 2/20* | (2006.01) | |
| *A01N 25/14* | (2006.01) | |
| *A01N 25/12* | (2006.01) | |
| *B07B 1/20* | (2006.01) | |

(52) U.S. Cl.
CPC .............. *A23K 1/16* (2013.01); *A61K 9/1682* (2013.01); *B01F 7/00041* (2013.01); *B01F 7/00116* (2013.01); *B01F 7/00175* (2013.01); *B01F 7/00208* (2013.01); *B01F 7/00708* (2013.01); *B01F 7/02* (2013.01); *B01F 13/1016* (2013.01); *B01J 2/10* (2013.01); *B01J 2/12* (2013.01); *B29C 67/02* (2013.01); *A01N 25/12* (2013.01); *A01N 25/14* (2013.01); *A61K 9/16* (2013.01); *A61K 9/1688* (2013.01); *A61K 9/1694* (2013.01); *B01F 7/04* (2013.01); *B01F 13/10* (2013.01); *B01F 13/1002* (2013.01); *B01F 13/1011* (2013.01); *B01F 13/1013* (2013.01); *B01J 2/20* (2013.01); *B01J 2/28* (2013.01); *B07B 1/20* (2013.01); *B29B 9/08* (2013.01); *B29B 13/10* (2013.01); *B29C 47/26* (2013.01); *B29C 47/36* (2013.01); *B29C 47/362* (2013.01); *B29C 47/38* (2013.01); *B29C 47/60* (2013.01); *B29C 67/08* (2013.01); *C22B 1/24* (2013.01); *C22B 1/2406* (2013.01)

(58) Field of Classification Search
CPC .... B01F 7/02; B01F 7/04; B01F 13/10; B01F 13/1002; B01F 13/1011; B01F 13/1013; B01F 13/1016; B29C 47/10; B29C 47/20; B29C 47/26; B29C 47/36; B29C 47/362; B29C 47/38; B29C 47/60; B29C 67/02; B29C 67/08; B29B 9/08; B29B 13/10; C22B 1/24; C22B 1/2406; A01N 25/12; A01N 25/14; A61K 9/1682; A61K 9/1688; A61K 9/1694; A61K 9/16

USPC ... 425/82.1, 197, 200, 205, 207, 222, 376.1, 425/377, 404, 447, 448, 332, 333, 130, 425/131.1, 135, 209
See application file for complete search history.

(56) References Cited

U.S. PATENT DOCUMENTS

| | | | | |
|---|---|---|---|---|
| 2,684,290 | A * | 7/1954 | Cruzan | B01J 2/16 23/313 FB |
| 2,776,828 | A * | 1/1957 | Marcellus | C01B 25/01 23/313 R |
| 2,835,583 | A * | 5/1958 | Higgins | A23C 21/04 426/289 |
| 2,860,598 | A * | 11/1958 | Gunter | B01J 2/14 118/19 |
| 2,948,948 | A * | 8/1960 | Duplin, Jr. | B01J 2/12 106/DIG. 1 |
| 2,979,421 | A * | 4/1961 | Rissman | C05C 9/005 159/11.2 |
| 3,017,662 | A * | 1/1962 | Marsh | C09C 1/58 23/314 |
| 3,056,162 | A * | 10/1962 | Fisher | C09C 1/58 23/314 |
| 3,231,638 | A * | 1/1966 | Henry | B01J 2/12 23/313 P |
| 3,263,592 | A * | 8/1966 | Hickey | A23N 17/002 118/19 |
| 3,277,218 | A * | 10/1966 | Dollinger | C09C 1/58 264/117 |
| 3,304,355 | A * | 2/1967 | Pobst, Jr. | B01F 15/00253 23/313 R |
| 3,319,949 | A * | 5/1967 | Hanson | C22B 1/2406 266/160 |
| 3,337,913 | A * | 8/1967 | Heinz | B01J 2/12 425/313 |
| 3,406,426 | A * | 10/1968 | Pobst, Jr. | B01J 2/10 264/117 |
| 3,584,098 | A * | 6/1971 | Adams, Jr. | B01J 2/12 252/192 |
| 3,743,461 | A * | 7/1973 | Williams | B01J 2/00 264/310 |
| 3,771,971 | A * | 11/1973 | Capes | B01J 2/12 209/362 |
| 3,775,331 | A * | 11/1973 | Borrello | B01J 2/10 435/187 |
| 3,830,943 | A * | 8/1974 | Hix et al. | B01J 2/12 23/313 R |
| 3,981,659 | A * | 9/1976 | Myers | C09C 1/58 23/314 |
| 3,989,473 | A * | 11/1976 | Henderson | C09C 1/58 209/238 |
| 4,003,717 | A * | 1/1977 | Cass | B01J 2/10 159/25.1 |
| 4,028,040 | A * | 6/1977 | Waltrip | C10L 5/02 425/222 |
| 4,108,932 | A * | 8/1978 | Takewell | B01J 2/12 264/117 |
| 4,113,413 | A * | 9/1978 | Pietrusza | B01J 2/12 23/313 R |
| 4,237,814 | A * | 12/1980 | Ormos | B01J 2/003 118/24 |
| 4,241,001 | A * | 12/1980 | Lamond | B01J 2/12 264/117 |
| 4,246,220 | A * | 1/1981 | Lamond | B01J 2/10 264/117 |
| 4,842,790 | A * | 6/1989 | Nunnelly | B01J 2/12 118/303 |
| 4,997,357 | A * | 3/1991 | Eirich | C04B 2/063 106/DIG. 1 |
| 5,037,286 | A * | 8/1991 | Roberts | B01J 2/12 106/709 |
| 5,100,510 | A * | 3/1992 | Bianchi | B01J 2/10 159/11.2 |

(56) References Cited

U.S. PATENT DOCUMENTS

| | | | | |
|---|---|---|---|---|
| 5,126,159 A * | 6/1992 | Manser | A21C 1/003 | 426/451 |
| 5,173,232 A * | 12/1992 | Holley | B01D 53/73 | 23/313 P |
| 5,186,539 A * | 2/1993 | Manser | A21C 1/003 | 366/85 |
| 5,585,180 A * | 12/1996 | Fadell | C03B 37/16 | 23/313 P |
| 5,610,444 A * | 3/1997 | Austruy | B01J 2/20 | 264/3.3 |
| 5,628,913 A * | 5/1997 | Modig | B01J 2/20 | 118/308 |
| 5,945,134 A * | 8/1999 | Strait | C03B 37/14 | 425/222 |
| 5,993,187 A * | 11/1999 | Manser | A21C 1/003 | 425/202 |
| 6,328,798 B1 * | 12/2001 | Bostrom | B01F 7/022 | 118/24 |
| 6,638,044 B2 * | 10/2003 | Rodriguez | A01N 25/12 | 264/4.3 |
| 6,659,756 B2 * | 12/2003 | Strait | C03B 37/14 | 425/222 |
| 8,105,742 B2 * | 1/2012 | Norikane | B01J 2/04 | 425/6 |
| 8,137,087 B2 * | 3/2012 | Norikane | B01J 2/04 | 310/311 |
| 8,323,793 B2 * | 12/2012 | Hamby | C09C 1/48 | 423/449.1 |
| 2004/0124555 A1 * | 7/2004 | Jadhav | B01J 2/20 | 264/117 |
| 2008/0286574 A1 * | 11/2008 | Hamby | C09C 1/48 | 428/402 |
| 2009/0110766 A1 * | 4/2009 | Thom, Jr. | B30B 11/202 | 425/222 |
| 2010/0119638 A1 * | 5/2010 | Allis | B30B 11/202 | 425/222 |
| 2012/0247164 A1 * | 10/2012 | Dahms | C05D 3/00 | 71/8 |
| 2013/0248625 A1 * | 9/2013 | Arnau Villanova | B02C 17/18 | 241/5 |

* cited by examiner

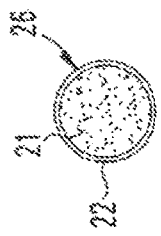
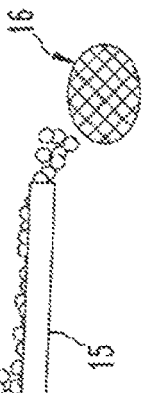
Fig. 2
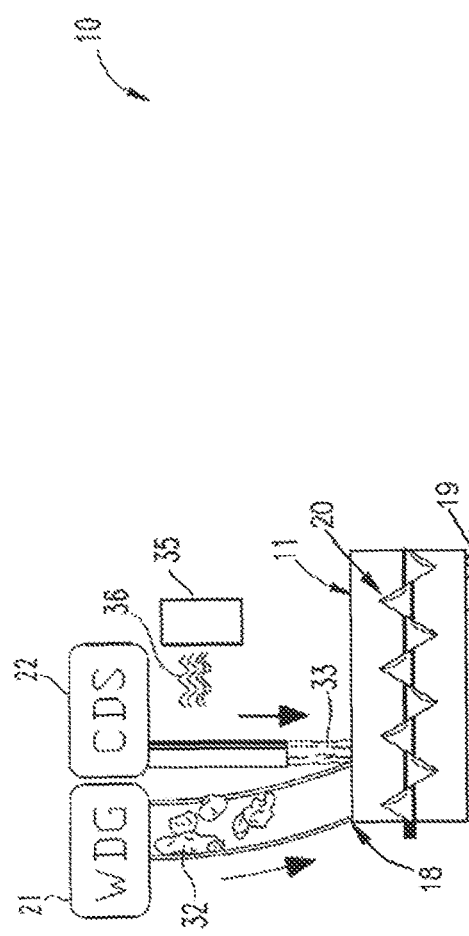
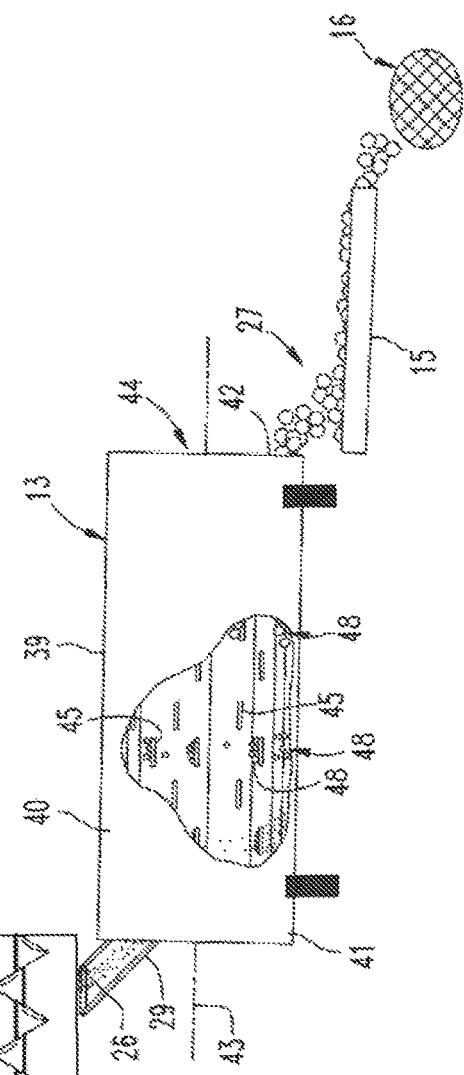
Fig. 1

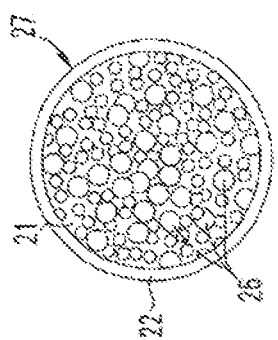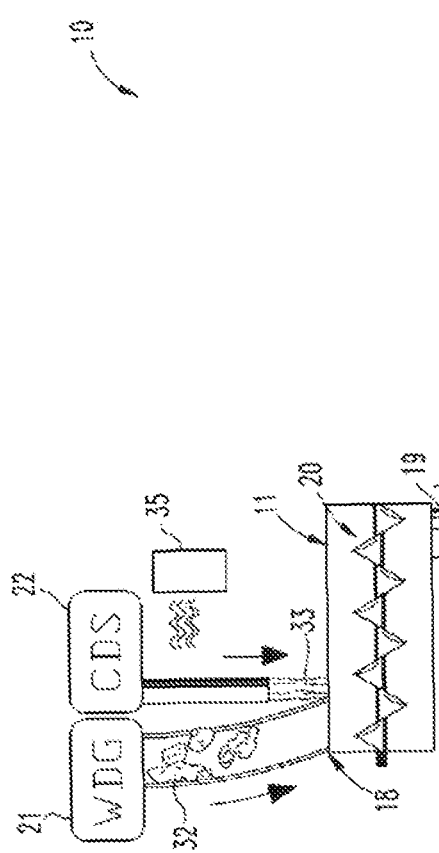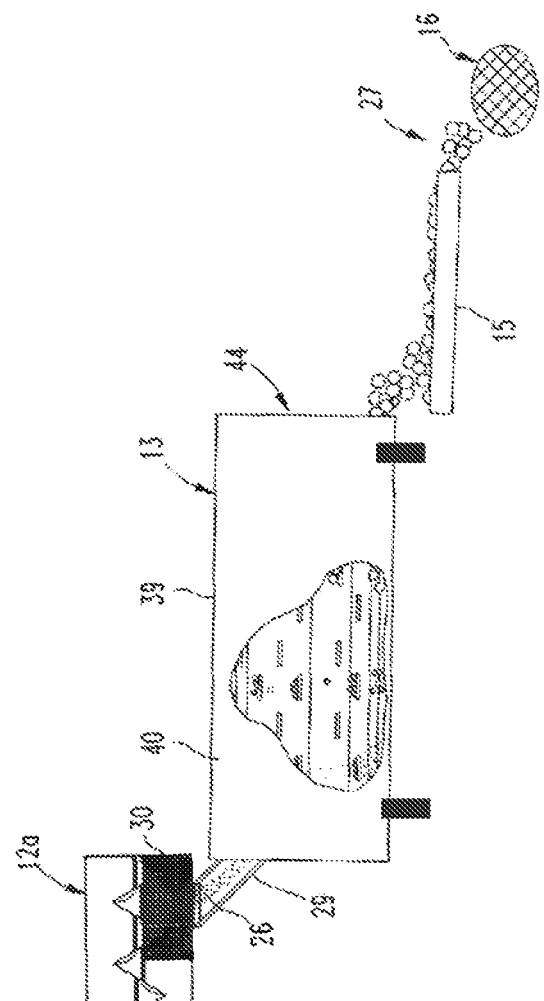

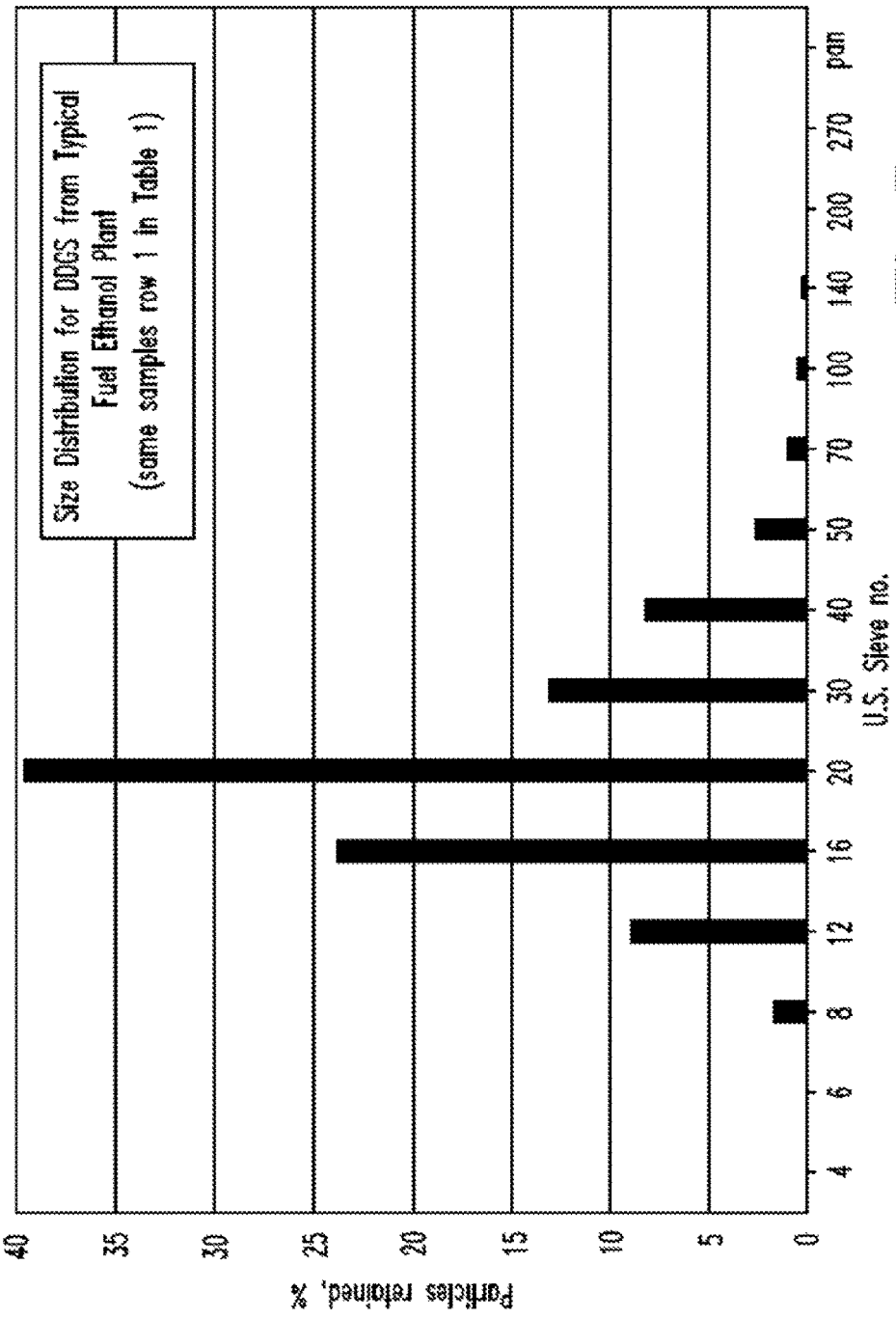

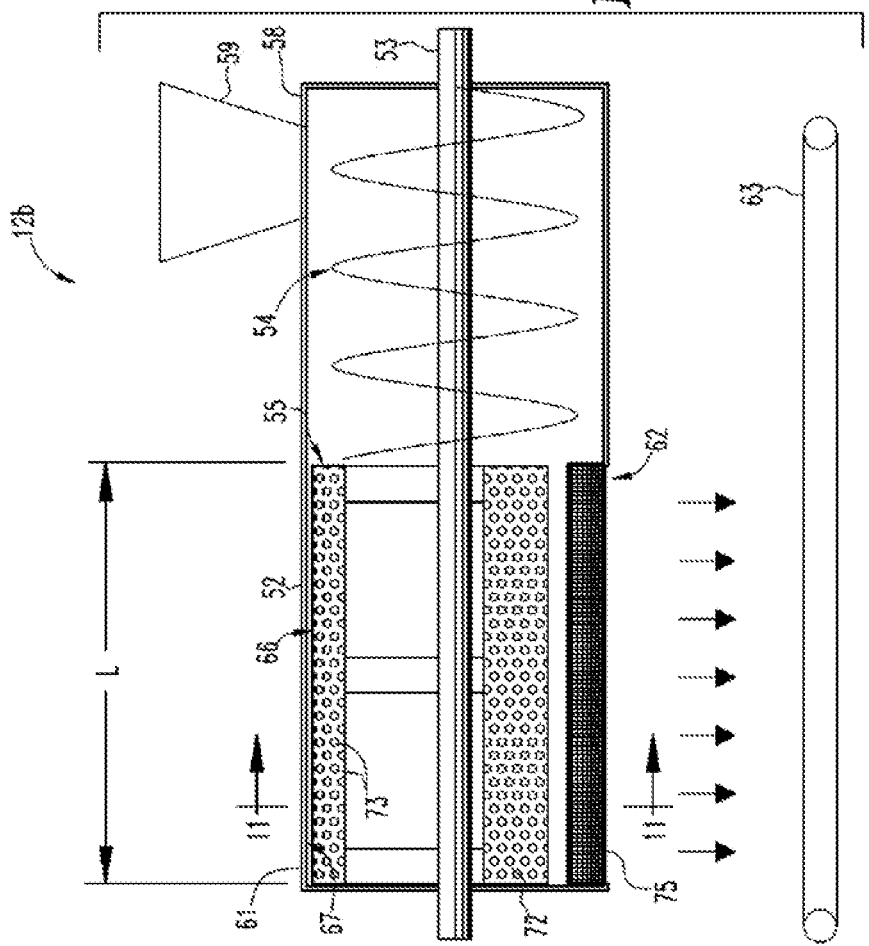
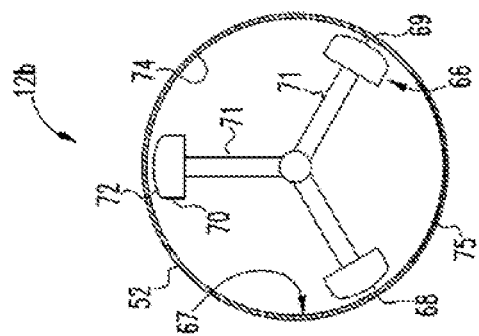

APPARATUS AND METHOD FOR PRODUCING BIOBASED CARRIERS FROM BYPRODUCTS OF BIOMASS PROCESSING

REFERENCE TO RELATED APPLICATIONS

This application is a division patent application of U.S. patent application Ser. No. 13/106,515 filed May 12, 2011, now issued as U.S. Pat. No. 9,272,468, which is a continuation-in-part of U.S. patent application Ser. No. 12/418,565 filed Apr. 3, 2009 (Now U.S. Pat. No. 8,118,582), which claims priority from U.S. Provisional Application No. 61/042,046 filed Apr. 3, 2008, which applications are hereby incorporated by reference in their entireties.

FIELD OF THE INVENTION

The present invention relates to the field of biological and chemical product dispersion, and more particularly, to biobased carriers and the apparatus and method of manufacturing same for dispersal of themselves and of biological and chemical molecules carried thereby.

BACKGROUND OF THE INVENTION

Control of insect pests, rodents of non-desirable plants is typically achieved through the use of pesticides. Along with fertilizers, such pesticides, including fungicides, insecticides, rodenticides, plant growth regulators, enzymes and other similar products, are often dispersed via spherical, biobased pellets or granules that are used as carriers for such biological or chemical agents.

Biobased carriers made from renewable feedstocks include corn, soybean and wheat, but supplies and costs of such feedstocks can fluctuate greatly with the growing world market and the discovery of alternative uses therefor. For instance, corn cobs, which are used for the manufacture of the pesticide carrier, DG Lite®, are in increasing demand in the field of ethanol production. Consequently, the supply of corn cobs for DG Lite® is diminishing and the cost is rising. What is needed is an alternative source for biobased carriers for pesticides, fertilizers, and other applications.

SUMMARY OF THE INVENTION

The present invention relates to the production of custom designed spherical dry pellets (granules) from wet distillers grains and gluten feed and gluten meal, coproducts of dry-grinding/dry milling and wet milling, respectively, for fuel ethanol and starch production from starchy grain feedstocks like corn, sorghum (milo), and wheat, etc. and methods of their preparation (production) using a rotary drum dryer or rotating drum granulator. Custom designed spherical dry pellets here refers to pellets that can be produced to a custom desired diameter and internal structure as determined by their end use. Such pellets utilize liquid binders from corn ethanol production, vis-a-vis condensed distillers solubles or thin stillage, glycerol (glycerine) or polymer. When wet distillers grains are blended with condensed distillers solubles, the resultant product is dried distillers grains with solubles (DDGS). The aforementioned pellets could also be produced for the sole purpose of improving the bulk physical and flow properties of distillers grains with solubles (DDGS) sold as livestock feed or as carriers to disperse biological or chemical molecules such as agrochemicals (pesticides for turf or crop applications and grain protectants, rodent baits, etc.) or enzymes. The invention contemplates both the apparatus and method for producing custom designed DDGS pellets as well as the pellets produced thereby. The method contemplates DDGS, gluten feed, gluten meal and other biomass pellet production from wet distillers grains from corn or other starchy grains (such as sorghum, wheat, etc.) using dry-grind processing, dry-fractionation, wet milling or similar processes.

In one embodiment, an apparatus for producing biobased carriers for dispersal of biological and chemical molecules includes a premixer having a cavity for receiving a coproduct of a wet biomass process and a binder and being operable to premix the coproduct and binder to produce a substantially homogeneous DDGS mixture; a high shear mixer having a receptacle for receiving the DDGS mixture and being operable to shear mix the mixture and produce very small DDGS particles; and an agglomerator having an interior chamber sized and configured to receive and transform the DDGS particles into substantially spherical DDGS pellets.

It is an object of the present invention to provide an improved method and apparatus for producing biobased carriers for pesticides, fertilizers, and other applications.

Other objects and advantages will become apparent from the following description of the preferred embodiment of the invention.

BRIEF DESCRIPTION OF THE DRAWINGS

FIG. 1 is a schematic view of an apparatus 10 for producing biobased carriers from byproducts of biomass processing in accordance with one embodiment of the present invention.

FIG. 2 is a cross-sectional view of a nucleation enhanced particle 26 created by apparatus 10 for producing biobased carriers from byproducts of biomass processing of FIG. 1.

FIG. 3 is a schematic view of an apparatus 10 for producing biobased carriers from byproducts of biomass processing in accordance with another embodiment of the present invention.

FIG. 7 is a graph showing the particle size distribution for pellets produced in typical fuel ethanol plants.

FIG. 8 is a cross-sectional view of a pellet 27 created by apparatus 10 for producing biobased carriers from byproducts of biomass processing of FIG. 1.

FIG. 10 is a side, cross-sectional view of an alternative embodiment of high shear mixer 12b of the apparatus 10 of FIG. 3.

FIG. 11 is a cross-sectional view of the high shear mixer 12b of FIG. 10 taken along the lines 11-11 and viewed in the direction of the arrows.

DESCRIPTION OF THE PREFERRED EMBODIMENT

Figure 5:
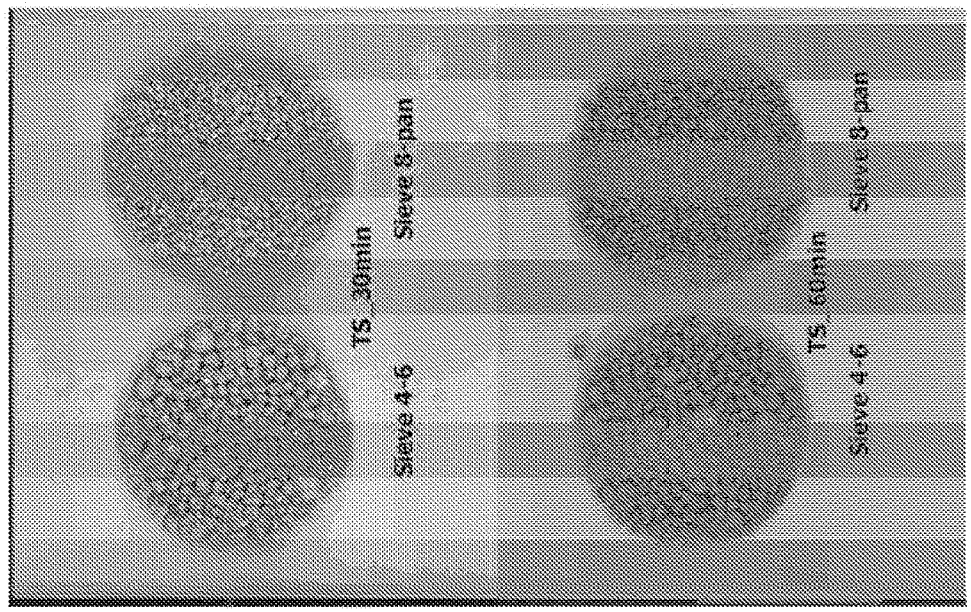
FIGS. 4 and 5 are plan views of custom sized spherical pellets produced by apparatus 10 for producing biobased carriers from byproducts of biomass processing of FIG. 3.

For the purposes of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described processes, systems or devices, and any further applications of the principles of the invention as described herein, are contemplated as would normally occur to one skilled in the art to which the invention relates.

The present invention relates to the production of size specific dispersible pellets that can be used as carriers for both chemical and biological agents such as enzymes, pesticides, herbicides, fungicides, rodent bait poison and the like, animal vaccinations, animal medications and animal supplements, as well as for dispersing nutrients through this medium. Size specific here means that the pellets can be made to a desired, reasonably consistent, substantially spherical shape. Because the pellets can be made to custom size (500 to 6000 microns geometric mean size), they can thus possess a range of bulk physical properties that correlate to particle size. Although smaller pellets could be produced, if produced as discussed below from particles having a size of about 300 to 500 microns, the pellets will generally be formed starting at about 1000 microns in diameter.

Referring to FIG. 1, there is shown schematically an apparatus 10 for producing biobased carriers from byproducts of biomass processing in accordance with one embodiment of the present invention. Apparatus 10 generally includes a premixer 11, a high shear mixer 12, and an agglomerator 13. Apparatus 10 may further include a cooling bed 15 and/or classifier 16. Apparatus 10 generally operates to (1) blend in premixer 11 a combination of wet biomass processing coproduct 21 and a binder 22, producing DDGS (dried distillers grains with solubles) paste 24; (2) shear mixing in high shear mixer 12 the DDGS paste 24 from premixer 11 to form nucleation enhanced particles (NEPS) 26; and, (3) agglomerating in agglomerator 13 the NEPS 26 from high shear mixer 12 to form desired sized biobased carriers or pellets 27.

Wet biomass processing coproduct 21 contemplates substantially any wet coproduct from a biomass processing operation such as, and without limitation, those resulting from the fermentation of starchy grain or cellulose feedstocks to make alcohol (as in distilleries); the fermentation of lignocelluloses to make ethanol; and, the fermentation of pre-fractionated grain to make ethanol. As used herein, coproduct includes any of the intended, secondary and/or unintended products of the biomass processing operation. One preferred coproduct 21 is wet distillers grain (WDG) 32 (known in distilleries as brewers grain), which is a coproduct of fuel ethanol production from starchy grain feedstocks like corn, sorghum (milo), and wheat. Coproduct 21, to be suitable for processing by apparatus 10, is contemplated to be a wet feedstock having a 50%-70% moisture content (wet basis). Some coproducts 21 may fall within this desired moisture content range directly after the operation that produced them, but others may require an additional drying step or the addition of a dry finely ground feedstock, such as a polymer, a biomass, etc. to achieve the desired 50-70% moisture content range.

Such additional drying step is performed by any suitable dryer operable to dry the coproduct to the desired moisture content and may include a rotating drum dryer and/or a fluidized conveyor bed.

Binder 22 is contemplated to include condensed distillers solubles (CDS) (also known as "the syrup"), thin stillage or glycerol (glycerine) or polymer. Other binders may be used instead, so long as they achieve the desired internal granule structure, nucleation, coalescence and layering during pellet growth, as described herein. Liquids without a sugar, starch or polymer component would likely be ineffective or at least substantially less effective as a suitable binder. One preferred binder is the CDS, which flows better when heated. One embodiment of apparatus 10 therefore includes a heater 35 operable to heat at 36 the CDS so it will readily flow into premixer 11. If this operation is done in an ethanol plant, distillery or similar structure, heating of the syrup will not be necessary since it comes hot from the evaporator.

Premixer 11 is a horizontal, trough type mixer having an inlet 18, and outlet 19, and a cavity (not shown) with one or more stirring elements 20 (e.g. stirring arms, screws, paddles or the like) operable in the cavity to receive and evenly mix target materials to a paste state. More particularly, the output DDGS paste 24 has a granulated cookie-dough or wet sand-type consistency (a homogeneous, granular wet solid) and is directed by a chute device (like the one at 29) or other suitable structure or positionment to the inlet (not shown) of high shear mixer 12. Premixer 11 may comprise any other suitable device capable of receiving and mixing the received materials to a substantially homogeneous state.

In one embodiment, high shear mixer 12 is a commercially available high shear mixer which, upon receipt of DDGS paste 24 in a cavity or similar mixture receiving receptacle, mechanically declumps and pulverizes it, or shear mixes it. That is, high shear mixer 12 breaks up the DDGS paste constituents to such a small degree that very small DDGS particles are formed that consist of (wet biomass processing) coproduct particles 21 that are coated with a thin film of binder 22 (such as CDS) (FIG. 2). These resulting DDGS particles are nucleation enhanced particles (NEPS) 26, which are directed out of high shear mixer 12 via a suitable chute device 29 or other suitable structure or positionment to the inlet (not shown) of agglomerator 13. The NEPS 26 are in the range of between about 300 to 500 microns in diameter. While they could be larger, the high stress shearing action of high shear mixer 12 will typically uniformly create NEPS in this range, which contributes to the particular agglomeration and resulting pellet production of the present invention.

Alternative embodiments are contemplated (FIG. 3) wherein high shear mixer 12a comprises a trough type mixer with one or more stirring arms, screws, paddles or the like, or any similar device, and has a screen 30 across which the DDGS paste 24 is forcibly moved or rubbed (by an arm, screw or paddle or the like) to shear mix the subject paste 24. DDGS paste 24 particles sufficiently broken down thereat, that can pass through the mesh size of screen 30, constitute the desired NEPS and pass out of high shear mixer 12a and are directed via chute device 29 to agglomerator 13.

Referring to FIGS. 10 and 11, there is shown an alternative embodiment high shear mixer 12b. High shear mixer 12a generally includes a housing 52, a central shaft 53, an auger 54 and a high shear mechanism 55. Housing 52 is generally cylindrical and includes at its entry end 58 an inlet hopper 59 (the inlet) configured to receive the DDGS paste 24 from premixer 11 and direct it to the inside (receptacle) of the housing. Housing 52 also defines at its opposite, exit end 61 an exit opening 62 (the outlet) through which the DDGS particles exit housing 52 for delivery to the agglomerator 13 via chute device 29 (FIG. 3) or, alternatively, belt conveyor 63 (FIG. 10). Central shaft 53 is supported for rotation by the opposing ends of housing 52 and is driven by an appropriate motor (not shown). Motors (for driving movable components e.g. augers and the like in the mixers, conveyor belts, agglomerators, etc.), sensors (for sensing temperatures, rotational speeds, etc.), an external power source (for powering the motors, sensors, etc.), and any other components or accessories necessary or desired to support operation of the apparatus 10, though not shown, are naturally contemplated as part of apparatus 10 and are generally referred to as power means for controlling the operation of apparatus 10. The auger is shown diagrammatically at 54 and comprises any stirring arms, screws, paddles or the like mounted to rotate with and be driven by shaft 53 at the entry or exit ends 58 or 61, respectively, of housing 52, to receive DDGS paste 24 entering from hopper 59 and to drive the DDGS paste 24 into high shear mechanism 55. Auger 54 thus functions to drive the DDGS paste 24 to and into high shear mechanism 55, but also functions to continue to mix the DDGS paste 24 as it moves toward high shear mechanism 55.

High shear mechanism 55 generally includes a rotor 66 and a stator 67, the rotor being mounted to rotate with and be driven by shaft 53 and the stator 67 being the stationary component comprising and/or mounted to the housing 52. Rotor 66 here comprises three identical rubbing bars 68, 69 and 70 that are generally mutually parallel to shaft 53, radially spaced around shaft 53 and rigidly mounted to shaft 53 by a number of radial arms 71. Rubbing bars 68-70 have a length L that determines, in connection with other factors (such as the speed of rotation of shaft 53), how long the DDGS paste 24 is worked by high shear mechanism 55. Rubbing bars 68-70 also each include an outer surface 72 that, over at least some of its length L, is arcuate, having portions thereof that have the same or lesser radii of curvature than that of the interior surface 74 of housing 52, as seen in FIG. 11. In one embodiment, the outer surfaces 72 are also non-smooth over at least a portion, and preferably all of their lengths. In one embodiment, the other surfaces 72 may also define a plurality of bumps 73 or other non-smooth elements extending up or down from the otherwise substantially smooth surface 72 to enhance the shear created between rubbing bars 68-70 and the stator 67.

The stator 67 here includes both the inner surface 74 of housing 52 and a screen 75 (like screen 30 of FIG. 3) positioned to cover or fill all of opening 62. Rubbing bars 68, 69 and 70 are sized, configured and positioned relative to and the inside of housing 52 and to screen 75 to "work" the fluid (the DDGS paste 24). Screen 75 (and, generally, opening 62) is shown extending through about 85 degrees along the bottom of cylindrical housing 52 so that the ejected DDGS particles will fall downwardly to the belt conveyor 63 or similar transport apparatus. It is believed that opening 62 and its screen 75 should preferably extend about one third or about 120 degrees, and generally be centered along the bottom of cylindrical housing 52. The screen 75 is contemplated to be positioned with housing 52 so that screen 75 and the inner surface 74 have substantially the same radius of curvature and so that the DDGS material being sheared inside housing 52 will be retained as little as possible on a leading edge of the screen 75 or the structure of housing 52 that holds screen 75. In one embodiment, screen 75 has a mesh between about 3 mm and 4.5 mm, with a preferred mesh around about 3.2 mm, and the rubbing bars 68-70 are mounted so that their outer surfaces rotate about 4 mm to 10 mm away from inner surface 74 and screen 75. That is, there is a fairly close tolerance gap between the rotating rubbing bars 68-70 and the stationary inner surface 74 and screen 75. The screen mesh size and gap dimension between rubbing bars 68-70 and inner surface 74 may vary depending on the composition, density, moisture content and other characteristics of the DDGS paste 24 or other material being subjected to high shear mixing of high shear mixer 12*b*. The fluid (DDGS paste 24) is moved by rubbing bars 68-70 of rotor 66 along stationary inner surface 74 and screen 75, which creates flow and shear therebetween. In addition to the high shear action imparted to the DDGS material, when the DDGS material is forced along the screen 75, a portion thereof is forced (extruded) through the screen mesh along the bottom side of and out of housing 52. The composition and condition of the DDGS material at this stage of the process causes the exiting DDGS material to break off in small pellets or wads that typically are not spherical.

Alternative embodiments are contemplated wherein opening 62 and the screen 75 are not centered along the bottom of housing 52 and/or extend more or less than about 120 degrees about housing 52.

In one embodiment, housing 52 is about five feet long, and rubbing bars 68-70 are about three feet long (about 60 percent of the working portion of high shear mixer 12*a*).

Alternative embodiments are contemplated wherein high shear mixer 12 comprises any suitable device operable to shear mix the DDGS paste 24 and convert it into NEPS 26, including, for example a device providing ultrasonic cavitation to the paste 24, with or without additional rotor-stator mixing structure.

Agglomerator 13 comprises a rotary drum dryer 39. Rotary drum dryer 39 generally includes a cylindrical metal reactor, or drum 40 that is inclined at its inlet end 41 slightly from the horizontal. Drum 40 defines an interior chamber 44 sized and configured to receive and manipulate the NEPS 26. A heat and blower source (not shown) located at one end of drum 40 provides a heat flow to raise the temperature of and dry NEPS 26 as they pass through drum 40. The heat flow may be either cocurrent with or countercurrent to the direction of flow of NEPS 26 toward the drum outlet 42. As drum 40 rotates about its axis 43, the NEPS 26 therein are conveyed through the drum toward the outlet 42 at the lower end 49 of the drum. Lifters 45 extending inwardly on the inside of drum 40 raise the NEPS 26, carrying them to near the top of the drum 40 before allowing them to fall through the heated gas flowing therethrough. The drying heat is contemplated to range from 400° F. to 1000° F., but this value may vary depending on whether the heat flow is cocurrent or countercurrent, as well as on the other parameters attendant to the desired size of the resulting DDGS pellets 27.

The drum rotation and heat flow act on the NEPS 26 to cause a nucleation, coalescence, layering and drying of the NEPS 26. That is, two or more NEPS 26, with their still wet outer film coating of CDS 33 coalesce to form a single body and, as drum 40 with its lifters 45 rotates, numerous such bodies (as at 48) form, each comprising multiple NEPS 26.

When these bodies 48 repeatedly rotate into a ball, they grow in diameter as they move toward outlet 42 until they harden and dry to form spherical pellets. In another embodiment, drum 40 is a drum granulator, having no lifters, which acts somewhat differently upon the coalescing bodies 48 of NEPS, still acting, however, to continuously roll the bodies into compacted, spherical DDGS pellets. Ultimately, the coalesced groups of NEPS 26 have formed individual, substantially equal and consistent diameter DDGS pellets 27 that comprise numerous, densely packed balls of the (now dry) wet biomass processing coproduct 21, each coated (within each pellet 27) with a film (or larger coating) of binder 22. (FIG. 8) Once the binder 22 has dried, coalescing and layering of the NEPS 26 (that is, of coproduct 21 and binder 22) has stopped, and the DDGS pellet 27 has reached its maximum size. Thus, the final size of DDGS pellet 27 can be substantially predetermined by: varying the parameters of agglomerator 13 (the rotational speed and number of revolutions of the drum 40 (time in the agglomerator) and the speed, direction and temperature of heat flow therethrough); the inclination of drum 40; the number and configuration of lifters 45 within drum 40 (or absence of the lifters, as in a drum granulator); and, the composition and amount of the binder 22 (here, condensed distillers solubles (CDS) 33) and, to a lesser extent, of the coproduct 21 (here, wet distillers grain (WDG) 32). Thus, for example, the greater the percentage of the binder (CDS 33) versus the starting biomass coproduct (WDG 32), the longer it will take the coalescing NEPS 26 to dry, and the more NEPS 26 will join together as a pellet and the larger the diameter of the pellet 27.

It is noted that while a faster drying time may achieve a certain pellet diameter by specifically terminating further mutual adhesion and coalescence, such earlier than average drying time may leave the core coproduct 21 (e.g. wet distillers grain (WDG)) with more moisture than desired, especially if drum granulators with no heat addition are used. Additional heating, such as before cooling bed 15, by any suitable means is contemplated to remove additional moisture, as desired.

Alternatively, one or more of the other factors affecting pellet size can be adjusted to attain both desired pellet size and overall moisture content. In one embodiment, pellets of 10% moisture content or below are desired for normal feed augmentation.

Another characteristic of forming DDGS pellets 27 from NEPS 26 is an increased density due to the coalescing of particles by rolling action to form a pellet. Each such rotation more closely packs the nucleated NEPS by layering together. In addition, the resulting, substantially spherical, more densely packed DDGS pellets exhibit superior flow characteristics over less dense and more irregularly shaped DDGS materials.

Alternative embodiments are contemplated wherein agglomerator 13 is a rotary drum without a heat source wherein, once the DDGS pellets are formed to the desired size, they are ejected from such rotary drum to a drying apparatus, which could be a drum dryer, a disc dryer, a conveyor or any other suitable drying device.

Upon exiting agglomerator 13, the DDGS pellets 27 are cooled using fluidized cooling bed 15, a rotary drum cooler (not shown) or other suitable cooling device. Thereafter, the DDGS pellets 27 exit the cooler 15 and pass through a suitable classifier 16 to sort the pellets into their various size categories. In one embodiment, classifier 16 is gravity table, a vibrating device that sorts particles into various size categories. In another embodiment, classifier 16 is a vibrating screening device of multiple, stacked and increasing mesh size screens with or without elutriation to remove fine particles. The smaller the pellet, the farther down it falls through the decreasing screen hole sizes until it exits by virtue of failing to pass through a particular screen size.

In one embodiment, apparatus 10 operates to produce custom designed biobased carriers from wet biomass processing coproduct 21 and binder 22 as follows: wet distillers grains (WDG) 32 and condensed distillers solubles (CDS) 33 are admixed at a percent weight/weight ratio of between 70:30 and 85:15 to premixer 11. Premixer 11 completes the preliminary mixing and outputs the resulting blended mixture as DDGS 24 paste into high shear mixer 12. The high shear mixer 12 shear mixes the DDGS paste 24, producing nucleation enhanced particles (NEPS) 26, which are then directed into agglomerator 13. Agglomerator 13 rotates and injects a drying airflow, which results in mutual coalescence, nucleation and layering of the coproduct 21 and binder 22 (growth) until the binder 22 dries enough to cease adhering NEPS 26 together into a spherical pellet.

In one embodiment, the process of the present invention is ideally suited for application in existing ethanol plants that are most ideal, least cost centers for production of custom designed pellets. This is because in ethanol plants, there exists the feedstock, wet distillers grains and solubles (condensed distillers solubles or thin stillage) for pellet production. Additionally, rotary drum dryers, one of the major equipment units that is needed for drying of the pellets, are available in fuel ethanol plants for drying wet distillers grains, gluten feed and gluten meal. Grain ethanol plants (dry grind, dry milling and wet milling) are thus preferred sites for pellet production from wet distillers grains with solubles. In addition, cost savings would be realized in reduced wet feedstock transportation costs and in sharing already existing handling infrastructure in the fuel ethanol plants.

Figure 4:
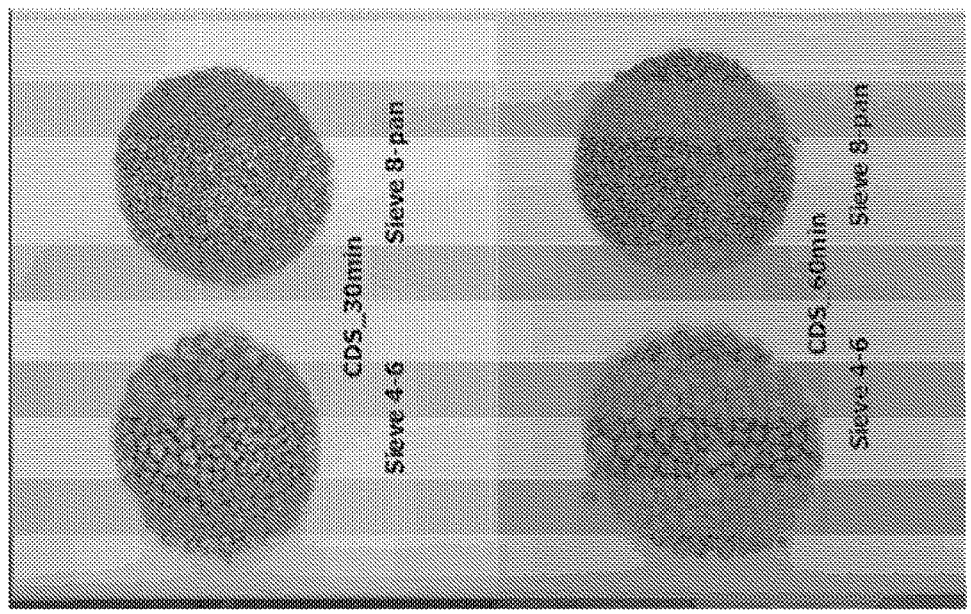

Results of bench-scale studies using the methodology described herein are shown in the scanned images of FIGS. 4 and 5. Specifically, custom designed spherical pellets were produced using wet distillers grains and with condensed distillers solubles (CDS) or thin stillage (TS) as a binder and for duration in the agglomerator 13 at 30 minutes and 60 minutes, as shown. The resulting custom sized spherical pellets (granules) are shown sorted to sieve 4-6 and sieve 8, respectively.

The present invention contemplates production of the DDGS pellets from coproducts from bioprocessing of any and all starchy grains, as well as feed meal from oil feeds, such as soybean meal, cotton seed meal, sunflower meal, gluten feed, gluten meal, and the like.

The term DDGS is used herein for the referenced resulting mixture, regardless of the composition of the initial wet biomass processing byproduct 21.

Referring to Table 1 below, there are shown physical properties tests for two different pellets produced in accordance with the present invention (Rows 2 and 3), which show more highly dense pellets than those from DDGS produced in typical fuel ethanol plants (Row 1) wherein wet distillers grain (WDG) is simply mixed with condensed distillers solubles (CDS) in a trough mixer and then dried in a rotary dryer. The first row represents control values from DDGS produced in the normal operation from corn fuel ethanol plants. The pellets produced in accordance with the present invention (Rows 2 and 3) and the control pellets (row 1) were all produced from the same WDG and CDS source.

Figure 6:
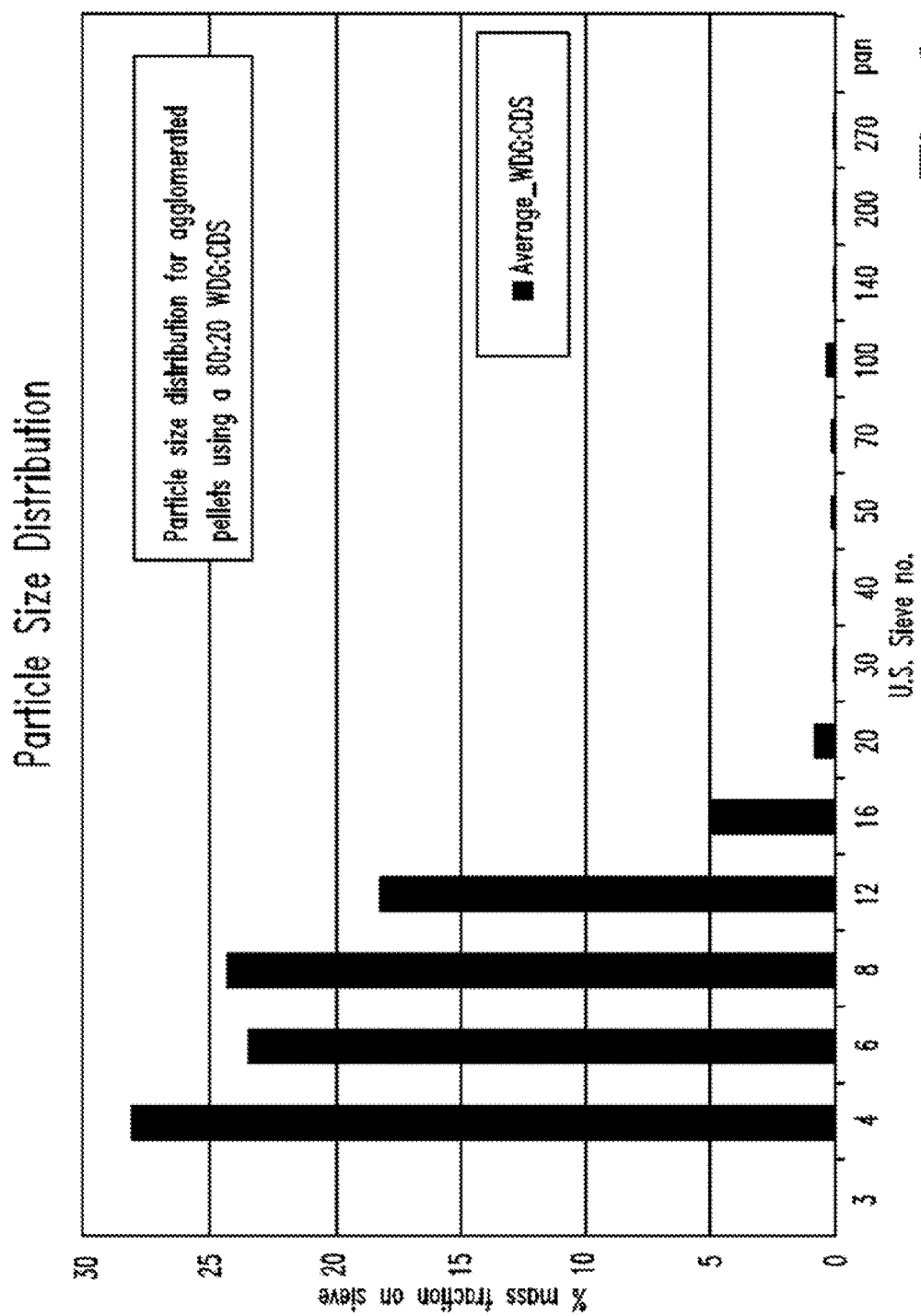
FIG. 6 is a graph showing the particle size distribution for pellets 27 produced by apparatus 10 for producing biobased carriers from byproducts of biomass processing of FIG. 3.

The custom designed pellets of the present invention achieve particle size diameters as high at 3300 microns compared to 910 microns ranges for regular DDGS. As shown in FIG. 6, the particle size distribution for pellets 27 of the present invention is skewed to the left, showing that the majority of the pellets were forced toward large sized pellet formation by the present process. Also, this reduced the spread of particle sizes, thus increasing uniformity.

The particle size distribution graph for typical DDGS pellets (i.e. row 1 of Table 1) will typically comprise a bell curve distribution (FIG. 7).

TABLE 1

Physical properties of custom designed biobased pellets from DDGS

| | | Bulk Physical Properties | | |
|---|---|---|---|---|
| Row | Treatments | Particle density (kg/m³) | Bulk density (kg/m³) | Geometric mean diameter (pm) |
| 1 | DDGS (from typical ethanol plant) | 1290.5 | 458.1 | 910 |
| 2 | WDG:CDS - 80:20 (% w/w) | 1309.0 | 529.3 | 3300 |
| 3 | WDG:TS - 80:20 (% w/w) | 1315.0 | 480.7 | 3160 |

In another bench-trial using the procedure and apparatus of FIG. 3, the resulting DDGS pellets 27 exhibited the characteristics shown in the fourth column of Table 2 below. The coproduct 21 was WDG; the binders were all CDS; and, the resulting pellets tested were sizes 8 and 12 sieve. The values compared in Table 2 to the subject DDGS carriers of the present invention are for currently available mineral and biobased pesticide carriers. As shown in Table 2, the DDGS carriers of the present invention had higher bulk density, comparable resistance to attrition and favorably low moisture content.

TABLE 2

A comparison of the physical properties of carriers.

| | Mineral Carriers | Biobased Carriers | DDGS Carriers |
|---|---|---|---|
| Bulk density (kg/m³) | 512-577 | 336 | 523.8 |
| Moisture content (%) | 3-10 | 8-10 | 4.9 |
| Resistance to attrition (%) | 75-90 | >99 | 84-93 |
| Angle of repose (°) | NA | NA | 31.5 |

Figure 9:
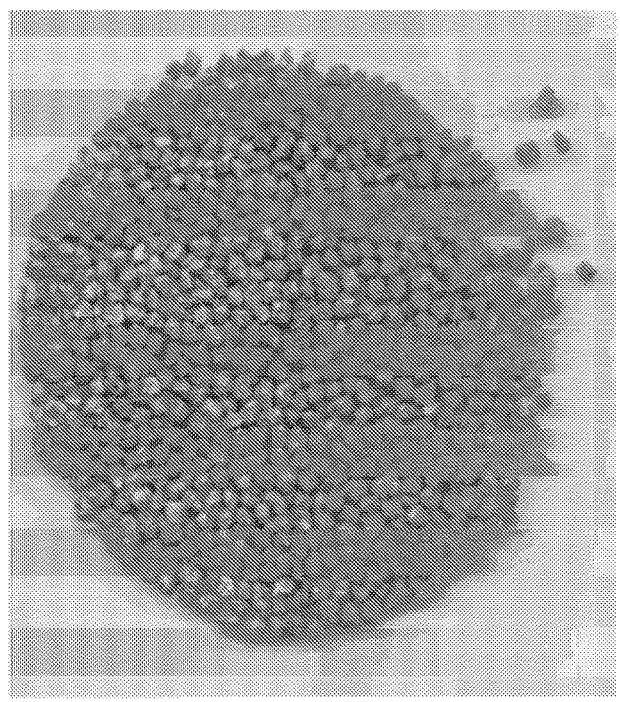
FIG. 9 is a plan view of custom sized spherical pellets produced by apparatus 10 for producing biobased carriers from byproducts of biomass processing of FIG. 3, the data for which is shown in Table 2.

The pellets produced in these tests (FIG. 9) used CDS as a binder and produced spherical pellets with a favorable range of physical particle and bulk characteristics.

One of the significant benefits of apparatus 10 is that it enables production of substantially consistent spherical biobased carrier pellets of any desired size within a broad 10 size range. Table 2 shows typical desired particle sizes for common carrier applications.

Agree and statement is suitable.

TABLE 3

Typical particle sizes of carriers.

| Application | Size range (microns): |
|---|---|
| Aerial | 2360-4750 |
| Lawn and Garden | 1180-2760 |
| In-furrow | 300-710 |
| Typical agricultural broadcast | 300-710 |
| Special pneumatic distribution | 180-425 |
| DDGS granules (size 8) | 2380-3350 |
| DDGS granules (size 12) | 1410-2380 |

The present invention is targeted at producing dry dispersible pellets from wet distillers grains and using condensed distillers solubles, thin stillage or a glycerol (glycerine) or polymer as a binder. The pellets are capable of carrying biologically and chemically active molecules which can be easily deployed and released to their activity sites. The release of the chemical or biological agents can be controlled by the design of the pellet's internal structure using a polymer matrix additive such as chitin, and the like. The pellets possess better granular properties, namely bulk physical and flow properties than the initial wet feedstock or DDGS. The aforementioned invention can also be used to produce consistent uniform sized spherical pellets with improved bulk physical and flow properties.

Apparatus 10 contemplates its input raw material to be any wet coproduct from a biomass processing operation. Alternative embodiments are contemplated wherein the input raw material is not a coproduct, but instead comprises an unprocessed biomass, such as ground dry biomass, wood saw dust, starch or other polymer. Also, chemical and/or biological matter may be added with the initial raw materials (coproduct 21 and binder 22) to modify the internal structure of the pellets for the purposes of their end use as biobased carriers of chemical and biological active ingredients. It is contemplated that the active ingredients of chemical or biological origins that are carried and dispersed by the biobased carrier mentioned herein can be added at the premixer 11 with other polymers used for controlling its release. In some cases it is contemplated that the DDGS pellets 27 will first be produced and the active chemical or biological ingredients will then be applied to the pellets using methods known in the industry such as spray coating, drum coating, and the like. Other applications are contemplated, such as for active ingredients of biological origin, wherein the active ingredient is inoculated into or onto the pellet which then grows on the pellet in the right temperature and relative humidity environments. Based on the description herein, some of the active ingredients will be either on the surface of the pellet (or granule) for immediate release or within the pellet for timed release.

Alternative embodiments are contemplated wherein the premixer 11 and high shear mixer 12 are combined into a common unit that receives and initially mixes the coproduct 21 and binder 22 and then performs a high shear mixing action to the premixed coproduct and binder material.

In another embodiment, lab scale batch granulation process was conducted, consisting of four steps: mixing, screen sizing (creating NEPS), granulation, and drying wherein the initial wet feed preparation included combining a predetermined amount of solids feed (WDG) and liquid binder (CDS). Laboratory temperature and relative humidity were maintained at 23±1° C. and 18±3% during experiments, respectively. The total combined weight of the initial wet feed was maintained at 600 grams (~3.2-3.4% load volume) across all trials. Before adding the CDS, the CDS was mixed thoroughly by hand and heated to 60±5° C. to ensure consistency, enhance flow, and improve dispersion during mixing. A hand-held mixer (Black and Decker Model MX 217, Towson, Md., USA) with two wire beaters was used to mechanically disperse the CDS throughout the WDG and initiate nucleation. Mixing was performed on the lowest speed setting for 2.5 minutes and remained constant for all trials. After mixing, the material was rubbed through a desired mesh size screen to break up lumps and provide a uniform feed size distribution. The resulting wet feed was carefully added to the drum for agglomeration using a vinyl mat to prevent accidental compaction during loading. In a commercial process, a belt conveyor is contemplated).

A brushed aluminum drum was designed and built for conducting batch granulation experiments. It consisted of a cylinder having a diameter of about 20.3 cm, fitted with two conical ends, having an overall length of about 56.2 cm and having a volume of about $12.7 \times 10^3$ cm³. Rotary action of the drum was produced by a bench-top tumbling system (C & M TopLine, Goleta, Calif., USA) that has two one inch steel bars providing a drum rotational speed of 39 RPM, 0.41 of the critical speed (nFR). An example of the calculation using equation 2.1 is given below:

$$N_{FR}=42.4(0.203)^{-0.5}=94.1\text{ RPM}$$

$$\text{Percent of } n_{FR}=39\text{ RPM}/(94.1\text{ RPM})=0.41$$

After granulating for the predetermined residence time, the charge was removed and placed onto trays and dried in a hot air oven (Model No. 21-250, Gilson Company Inc., Lewis Center, Ohio, USA) at a temperature of 125±5° C. for a time range of 45-60 minutes. Drying was monitored gravimetrically by weighing the trays until a mass representing a final moisture content of 10% was reached.

The highest granular yields (~80%) can be obtained at residence times between 2.5 and 10 minutes with 35% (wt/wt) binder (CDS) addition using the high solids (38% solids on a wet basis) content CDS and the small screen size opening (3.175 mm).

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

The invention claimed is:

1. A method for producing biobased carriers for dispersal of biological and chemical molecules, the method comprising:

providing an apparatus for producing biobased carriers, the apparatus including a premixer, a shear mixer, an agglomerator, and a power source for controlling an operation of the apparatus, the shear mixer having a cylindrical housing and a shear mechanism within the housing, the housing defining an inner surface and an opening, the shear mechanism comprising a screen covering the opening, a stationary stator, and a rotatable rotor disposed within the stator, the rotor comprising a shaft and a plurality of rubbing bars mounted and radially spaced around the shaft to rotate with the shaft, wherein each of the rubbing bars has an arcuate outer surface operable to move in a circumferential direction along an inner surface of the screen when the shaft rotates, wherein at least a portion of each respective arcuate outer surface defines a plurality of elements extending up or down from the respective arcuate outer surface to enhance shear created between the plurality of rubbing bars, the screen, and the inner surface of the stator;

adding a wet biomass processing coproduct and a binder into the premixer;

mixing the coproduct and the binder in the premixer to form a paste;

shear mixing the paste in the shear mixer by rotating the shaft thereof to create flow and shear between the plurality of rubbing bars, the screen, and the inner surface of the housing, force the paste along the screen in the circumferential direction thereof, and force and extrude the paste through the screen and out of the housing in the form of particles that are sufficiently broken down at the screen to pass through the screen; and agglomerating the particles with the agglomerator to form spherical biomass pellets.

2. The method of claim 1, wherein the providing step includes the shear mixer having drive means within the housing for receiving the paste from the premixer and forcing the paste into the shear mechanism.

3. The method of claim 1, wherein the providing step includes the screen having a mesh size between about 3 mm and 4.5 mm.

4. The method of claim 1, wherein the providing step includes the screen having a mesh size about 3.2 mm.

5. The method of claim 1, wherein the providing step includes the screen extending about 120 degrees about the housing.

6. The method of claim 1, wherein the providing step includes the stator comprising the inner surface of the housing.

7. The method of claim 1, wherein the providing step includes the plurality of rubbing bars having the outer surfaces spaced about 4 mm and 10 mm from the stator.

8. The method of claim 1, wherein the providing step includes the stator of the shear mechanism comprising the screen.

9. The method of claim 1, wherein the providing step includes the agglomerator being a rotary drum dryer having an interior chamber.

10. The method of claim 9, wherein the providing step includes the rotary drum dryer having lifters extending inwardly in the interior chamber.

11. The method of claim 1, wherein the adding step includes the wet biomass processing coproduct being wet distillers grain.

12. The method of claim 1, wherein the adding step includes the wet biomass processing coproduct having between about a 50% to 70% moisture content.

13. The method of claim 1, wherein the adding step includes the binder comprising at least one of condensed distillers solubles, thin stillage, glycerol and polymer.

14. The method of claim 13, wherein the adding step includes the binder being condensed distillers solubles.

15. The method of claim 14, wherein the providing step includes the apparatus further including heating means for heating the condensed distillers solubles before the condensed distillers solubles are added to the premixer.

16. The method of claim 1, wherein the adding step includes adding at least one of a dry feedstock, polymer and biomass to the premixer to lower a moisture content of the wet biomass processing coproduct to between about a 50-70% moisture content.

17. The method of claim 13, wherein the adding step includes adding at least one of a chemical agent and a biological agent.

18. The method of claim 17, wherein the adding step includes the at least one of the chemical agent or the biological agent being at least one of an enzyme, pesticide, herbicide, fungicide, rodent bait poison, animal vaccination, animal medication, animal supplement, and nutrients.

19. The method of claim 1, wherein the shear mixing step includes the particles having a diameter in the range of between about 300 to 500 microns.

20. The method of claim 1, wherein the adding step includes the binder being a liquid other than water.

* * * * *